United States Patent
Morris et al.

(10) Patent No.: US 7,323,193 B2
(45) Date of Patent: Jan. 29, 2008

(54) METHOD OF MAKING DEMINERALIZED BONE PARTICLES

(75) Inventors: John Morris, Beachwood, NJ (US); Lawrence A. Shimp, Morganville, NJ (US); Kenneth C. Petersen, Brick, NJ (US); Albert Manrique, Manalapan, NJ (US); David Kaes, Toms River, NJ (US); Nelson Scarborough, Andover, MA (US); Michael Dowd, Eastampton, NJ (US)

(73) Assignee: Osteotech, Inc., Eatontown, NJ (US)

( * ) Notice: Subject to any disclaimer, the term of this patent is extended or adjusted under 35 U.S.C. 154(b) by 661 days.

(21) Appl. No.: 10/433,588

(22) PCT Filed: Dec. 14, 2001

(86) PCT No.: PCT/US01/48384

§ 371 (c)(1),
(2), (4) Date: Jun. 5, 2003

(87) PCT Pub. No.: WO02/47732

PCT Pub. Date: Jun. 20, 2002

(65) Prior Publication Data

US 2004/0023387 A1 Feb. 5, 2004

(51) Int. Cl.
*A61K 35/32* (2006.01)
(52) U.S. Cl. ..................................... 424/549
(58) Field of Classification Search ............... 424/549, 424/548; 623/16, 18
See application file for complete search history.

(56) References Cited

U.S. PATENT DOCUMENTS

| 4,743,259 A | 5/1988 | Bolander et al. |
| 4,902,296 A | 2/1990 | Bolander et al. |
| 5,053,049 A | 10/1991 | Campbell |
| 5,073,373 A | 12/1991 | O'Leary et al. |
| 5,298,254 A | 3/1994 | Prewett et al. |
| 5,314,476 A * | 5/1994 | Prewett et al. ........... 623/23.63 |
| 5,507,813 A | 4/1996 | Dowd et al. |
| 5,607,269 A | 3/1997 | Dowd et al. |
| 5,846,484 A | 12/1998 | Scarborough et al. |
| 6,311,690 B1 * | 11/2001 | Jefferies .................... 128/898 |
| 2002/0107570 A1 * | 8/2002 | Sybert et al. ............ 623/13.17 |

FOREIGN PATENT DOCUMENTS

DE 179833 * 2/1905

OTHER PUBLICATIONS

The term "Substantially", Merriam-Webster Online Dictionary, at thw web- http://www.m-w.com, p. 1.*
Perez B.J. et al. Mechanical properties of a discontinuous random fiber composite for totally bioabsorbable fracture fixation devices, Paper presented in: Bioengineering Conference, 1995, Proceedings of the 1995 IEEE 21st Annual Northeast, May 22-23, 1995, pp. 55-56.*
USPTO Translation for the cited German patent DE 179,833 to Hunter J.R., pp. 1-3.*

* cited by examiner

*Primary Examiner*—Sandra E. Saucier
*Assistant Examiner*—Satyendra K. Singh
(74) *Attorney, Agent, or Firm*—Kenneth E. Levitt

(57) ABSTRACT

Demineralized bone particles are obtained by demineralizing whole bone and thereafter subdividing the demineralized bone to provide the demineralized bone particles.

10 Claims, No Drawings

METHOD OF MAKING DEMINERALIZED BONE PARTICLES

BACKGROUND OF THE INVENTION

This invention relates to a method of making demineralized bone particles useful in, or as, implants having a variety of orthopedic applications. More particularly, this invention relates to a method of making particles from demineralized bone that results in a greater yield of demineralized bone particles than that provided by prior art methods of producing such particles.

The manufacture of demineralized bone particles and compositions, materials and devices containing demineralized bone particles and their use in the repair of bone defects and for other orthopedic applications are known.

The microstructure of cortical bone consists of bundles, or fibers, of mineralized collagen that are oriented parallel to the long axis of the known methods for making demineralized bone particles involve subdividing sections of whole, i.e., mineralized, bone, e.g., by such mechanical operations as shredding, milling, shaving, machining, etc., to provide particles which are then demineralized, e.g., by treatment with acid. The resulting demineralized bone particles exhibit osteoinductive properties that make them useful as, or in, implants intended for use in bone repair and other orthopedic applications. One drawback of known methods of making demineralized bone particles is that only a portion of the bone stock, e.g., 45-65% by weight, will yield demineralized bone particles. In addition, because of the mechanical limitations of the bone milling machinery, e.g., the need to grip the bone stock in the jaws of the machine, only donor bone of a fairly substantial size, e.g., intact cortical shafts, can be used as to the source of the demineralized bone particles.

The limited amount of demineralized bone particles that is obtained by the prior art methods is of concern due to the limited availability of donor bone. At this time, regulations do not permit the pooling of donor bone material. Since the quantity of demineralized bone particles that can be obtained is limited both by the availability of donor bone and the size of the bone, there is a need for a method of making demineralized bone particles that is not subject to the constraints imposed by these limiting factors.

SUMMARY OF THE INVENTION

It is an object of the invention to provide a method of making demineralized bone particles which makes optimum use of donor bone.

It is a further object of the invention to provide a method of making demineralized bone particles that results in a greater yield of particles for a given quantity of whole bone compared to that provided by prior art methods.

It is yet another object of the invention to provide demineralized bone particles in the form of fibers or fibrous bundles of bone collagen by application of mechanical pressure to demineralized bone stock.

Further objects of the invention will be apparent to those skilled in the art in view of the above objects and the foregoing specification.

In keeping with these and related objects of the invention, there is provided a method of making demineralized bone particles which comprises demineralizing whole bone and thereafter subdividing the demineralized bone into demineralized bone particles.

In general, the yield of demineralized bone particles obtained by the method of this invention is significantly greater, e.g., from about 5 to about 20 wt. % greater, than that obtained by first subdividing the whole bone into mineralized bone particles and only thereafter demineralizing the mineralized bone particles to provide demineralized bone particles.

The term "particles" as utilized herein is intended to include relatively small bone pieces such as fibers, bundles of loosely connected fibers, threads, narrow strips, thin sheets, chips, shards, powders, etc., that possess regular, irregular or random geometries and which may, or may not be, completely separated from each other.

The expression "whole bone" as utilized herein refers to bone that contains its full naturally occurring mineral content and includes anatomically complete bones and sections thereof.

The term "demineralized" as used herein refers to bone containing less than about 95% of its original mineral context. The expression "fully demineralized" as used herein refers to bone containing less than about 5% of its original mineral context.

The terms "osteogenic" as used herein shall be understood to refer to the ability of a material or substance to induce new bone formation via the participation of living cells from within the substance and "osteogenesis" as the mechanism or result.

The terms "osteoinductive" as used herein shall be understood to refer to the ability of a material or substance to recruit cells from the host which have osteogenic potential and the ability to form ectopic bone and "osteoinduction" as the mechanism or result.

The terms "osteoconductive" as used herein shall be understood to refer to the ability of a material or substance or material to provide surfaces that are receptive to the growth of new host bone and "osteoconduction" as the mechanism or result.

The terms "autogenic", "allogenic" and "xenogenic" are used herein relative to the ultimate recipient of the bone tissue.

DETAILED DESCRIPTION OF THE INVENTION

The whole bone suitable for making the demineralized bone particles of this invention can be donor bone from any source. Thus, autogenic, allogenic or xenogenic bone can be used with autogenic and allogenic bone being preferred. An especially useful source of xenogenic tissue can be porcine, equine, or bovine. The bone can be cortical, cancellous or corticocancellous. The preferred bone is cortical allogenic bone, e.g., femur, tibia, fibula, radius, ulna, etc.

The method of this invention is applicable to whole bone in a variety of sizes. Therefore, the bone utilized as the starting, or stock, material will range in size from relatively small pieces of bone to bone of such dimensions as to be recognizable as to its anatomical origin. In general, the pieces or sections of whole bone stock can range from about 1 to about 400 mm, and preferably from about 5 to about 100 mm, in median length, from about 0.5 to about 20 mm, and preferably from about 2 to about 10 mm, in median thickness and from about 1 to about 20 mm, and preferably from about 2 to about 10 mm, in median width.

After the bone is obtained from the donor, it is processed, e.g., cleaned, disinfected, defatted, etc., using methods well known in the art. The entire bone can then be demineralized or, if desired, the bone can just be sectioned before demineralization. The entire bone or one or more of its sections is then subjected to demineralization in order to reduce the inorganic content to a low level, e.g., to contain less than about 10% by weight, preferably less than about 5% by weight and more preferably less than about 1% by weight, residual calcium.

Demineralization of the bone can be accomplished in accordance with known and conventional procedures. Demineralization procedures remove the inorganic mineral component of bone by employing acid solutions. Such procedures are well known in the art, see for example, Reddi et al., *Proceeding of the National Academy of Sciences of the United States of America* 69, pp.1601-1605 (1972), incorporated herein by reference. The strength of the acid solution, the shape and size of the bone and the duration of the demineralization procedure will determine the extent of demineralization. Generally speaking larger bone portions as compared to small particles will require more lengthy and vigorous demineralization. Guidance for specific parameters for the demineralization of different size bone can be found in U.S. Pat. No. 5,846,484, Harakas, Clinical Orthopaedics and Related Research, pp 239-251(1983) and Lewandrowski et al., *Journal of Biomedical Materials Research,* 31, pp. 365-372 (1996), each of which is incorporated by reference herein.

In a demineralization procedure useful in the practice of the invention herein, the bone is subjected to a defatting/disinfecting step that is followed by an acid demineralization step. A useful defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily at least about 10 to about 40 weight percent by weight of water (i.e., about 60 to about 90 weight percent of defatting agent such as alcohol) should be present in the defatting/disinfecting solution to produce optimal lipid removal and disinfection within the shortest period of time. A useful concentration range of the defatting solution is from about 60 to 85 weight percent alcohol or about 70 weight percent alcohol. An alternative or supplemental defatting solution is made from a surfactant such as Triton X-100 at a concentration of 0.1% to 10% in water. Following defatting, the bone is immersed in acid over time to effect demineralization. Acids which can be employed in this step include inorganic acids such as hydrochloric acid and organic acids such as peracetic acid. After acid treatment, the demineralized bone is rinsed with sterile water for injection to remove residual amounts of acid and thereby raise the pH.

Following demineralization, the bone is subdivided into demineralized bone particles of desired configuration and size. Useful for the subdivision of the demineralized bone are machines or instruments known to the arts of, e. shredding, milling, pressing, shaving, machining, extruding and/or cutting, of hard or brittle materials such as wood, plastics, soft metals, ceramics and the like. Particularly preferred are mills, including impact mills, grating mills, shearing mills and cutting mills. Many of the preferred instruments for the subdivision of the demineralized bone will fragment the demineralized bone, by cutting or separating the demineralized material in direction parallel to the underlying collagen fibers Particularly preferred types of equipment or machine useful for shredding, cutting hard or brittle materials such as wood, plastics, soft metals that can be used to subdivide the demineralized bone include impact mills, grating mills, shearing mills and cutting mills. Many preferred cutting and milling instruments and or machine will fragment the demineralized bone, by cutting or separating the demineralized material in direction parallel or nearly parallel to the underlying collagen fibers. Mills, presses and extruders are particularly useful in this regards.

An impact mill has blunt rotors or swinging hammers that move at high speed and subdivide the demineralized bone stock by impacting upon the bone shattering it into fragmentary particles. The bone tends to shatter along the lines of the natural collagen bundles constituting the microstructure of the bone. Similar mills with sharp cutting rotors tend to chop the bone into somewhat symmetric particles as opposed to the fibrous particles obtained with an impact mill. Impact speed is a factor that influences the result. Too low a speed may cause the bone to plastically deform rather than shatter into particles as required. This and similar factors involved in the operation of a particular type or model of impact mill to provide demineralized bone fibers can be optimized employing routine experimentation.

A shearing mill subdivides demineralized bone stock by tearing the bone apart. The tearing action tends to preferentially break the bone apart at its weakest point. The junctions between demineralized collagen bundles represent weak points and the result is the production of fiber type particles.

The spindle element of a lathe can be adapted to carry a rotary grinding wheel whose circumferential surface is studded with projecting cutting elements. As the bone stock is pressed against the rotating wheel, the cutting elements produce fiber-type particles. In this type of particle-forming operation, the resulting fibrous particles are not separated along the lines of natural collagen bundles.

Still other apparatus useful in milling bone particles according to the invention includes mills available from IKA® Works (Wilmington, N.C.) such as the model A 10 IKA-Analytical Mill or the model M 20 IKA-Universal Mill. Such mills have cooling connections and are suitable for the grinding of hard and brittle substances with a maximum grain size of 6-7 mm. It has been determined that a stainless steel star-shaped cutter provides particles of a useful size. Other milling machines useful in the practice of the invention herein include drum cutter bone mills such as those available from Tracer Designs, Inc. (Santa Paula, Calif.), e.g., its bone mill model BM1000.

A particularly effective method for subdividing demineralized bone stock is to subject the bone to pressing. The simplest pressing technique is to apply pressure to the unconstrained demineralized bone. Examples include pressing the bone using a mortar and pestle, applying a rolling/pressing motion such as is generated by a rolling pin, or pressing the bone pieces between flat or curved plates. These flattening pressures cause the bone fibers to separate. Unlike the prior art method for making fibers from mineralized bone, pressing demineralized bone in accordance with the present invention provides intact natural bone collagen fibers. (not composite fibers made from joined short fiber sections) that can be as long as the fibers in the demineralized bone stock from which they were obtained.

Another pressing technique involves mechanically pressing demineralized bone which is constrained within a sealed chamber having a hole (or a small number of holes) in its floor or bottom plate. The separated fibers extrude through the holes with the hole diameter limiting the maximum diameter of the extruded fibers. As with the unconstrained pressing method, this constrained technique results in fibers that are largely intact (as far as length is concerned) but separated bone collagen bundles.

In a combined unconstrained/constrained pressing technique that results in longer fibers by minimizing fiber breakage, the demineralized bone is first pressed into an initially separated mass of fibers while in the unconstrained condition and thereafter these fibers are constrained within the sealed chamber where pressing is continued.

In general, pressing of demineralized bone to provide demineralized bone particles can be carried out at from about 1,000 to about 40,000 psi, and preferably at from about 5,000 to about 20,000 psi.

Depending on the procedure employed for producing the demineralized bone particles, one can obtain a mass of bone particles in which at least about 80 weight percent, preferably at least about 90 weight percent and most preferably at least about 95 weight percent, of the particles possess a median length of from about 2 to about 300 mm or greater, preferably a median length of from about 5 to about 50 mm, a median thickness of from about 0.5 to about 15 mm, preferably a median thickness of from about 1 to about 5 mm, a median width of from about 2 to about 35 mm, preferably a median width of from about 2 to about 20 mm and a median length to thickness ratio and/or a median length to width ratio of from about 2 to 200, preferably from about 10 to about 100. If desired, the mass of bone particles can be graded or sorted into different sizes, e.g., by screening, and/or any less desirable size(s) of bone particles that may be present can be reduced or eliminated.

At this time, depending upon their intended final usage, the demineralized bone particles can be utilized as is or stored under aseptic conditions, advantageously in a lyophilized or frozen state, for use at a later time.

The demineralized bone particles of this invention find use as, or in implants, for a variety of orthopedic procedures where they participate in the bone healing/repair process through one or more mechanisms such as osteogenesis, osteoinduction and osteoconduction. The demineralized bone particles can be used as is, or formed into a variety of product types such as a gel, putty, or sheet. The demineralized bone particles can optionally be admixed with one or more substances such as adhesives, fillers, plasticizers, flexibilizing agents, biostatic/biocidal agents, surface active agents, binding and bonding agents, and the like, prior to, during, or after shaping the particles into a desired configuration. Suitable adhesives, binding agents and bonding agents include acrylic resins, cellulosics, bioresorbable polymers such as polyesters, polycarbonates, polyarylates and polyfomarates. Specifically, tyrsine, polycarbonates, tyrosine polyarylates, polyglycolides, polylactides, glycolide-lactide copolymer, etc. Suitable fillers include bone powder, demineralized bone powder, hydroxyapatite, etc. Suitable plasticizers and flexibilizing agents include liquid polyhydroxy compounds such as glycerol, monacetin, diacetin, etc. Suitable biostatic/biocidal agents include antibiotics, providone, sugars, etc. Suitable surface-active agents include the biocompatible nonionic, cationic, anionic and amphoteric surfactants.

If desired, the demineralized bone particles can be modified in one or more ways, e.g., their protein content can be augmented or modified as described in U.S. Pat. Nos. 4,743,259 and 4,902,296, the contents of which are incorporated by reference herein. Any of a variety of medically and/or surgically useful substances can be incorporated in or associated with the bone particles either before, during or after their formation. Thus, e.g., one or more of such substances can be introduced into the demineralized bone particles, e.g., by soaking or immersing the bone particles in a solution or dispersion of the desired substance(s).

Medically/surgically useful substances which can be readily combined with the demineralized bone particles of this invention include, e.g., collagen, insoluble collagen derivatives, etc., and soluble solids and/or liquids dissolved therein, e.g., antiviricides, particularly those effective against HIV and hepatitis; antimicrobials and or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; biocidal/biostatic sugars such as dextrose, glucose, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with fragments; synthesizers; enzymes such as collagenase, peptidases, oxidases, etc.; polymer cell scaffolds with parenchymal cells; angiogenic drugs and polymeric carriers containing such drugs; collagen lattices; antigenic agents; cytosketetal agents; cartilage fragments, living cells such as chondrocytes, bone marrow cells, mesenchymal stem cells, natural extracts, tissue transplants, bone, demineralized bone powder, autogenous tissues such blood, serum, soft tissue, bone marrow, etc.; bioadhesives, bone morphogenic proteins (BMPs), transforming growth factor (TGF-beta), insulin-like growth factors (IGF-1) IGF-2); platelet derived growth factors (PDGF); growth hormones such as somatotropin; bone digestors; antitumor agents; immuno-suppressants; permeation enchancers, e.g., fatty acid esters such as laureate, myristate and stearate monoesters of polyethylene glycol, enamine derivatives, alpha-keto aldehydes, etc.; and, nucleic acids. The amounts of such optionally added substances can vary widely with optimum levels being readily determined in a specific case by routine experimentation.

The method of this invention will be better understood by way of example. As is the case throughout this application, all parts are by weight unless otherwise specified. The examples are provided as a means for explaining the invention herein and are not intended to limit the invention in any way.

EXAMPLE 1

A right diaphysis (99 g) of human donor origin was divided lengthwise into four sections. The total weight of all the sections was 94 g. The bone sections were placed in a 2-liter container along with 1410 ml of a 0.6 N HCl solution. After approximately 6 hours the solution was removed and replaced with another 1410-ml portion of the acid solution. The bone sections and second aliquot of acid solution were subjected to mild vortexing with a magnetic stirrer for two days. The bone sections were demineralized until they were completely translucent without any visible mineralized areas indicating substantially complete demineralization. The demineralized bone sections were then rinsed with water until the pH of the rinse water was above 4.0. The demineralized bone sections were then soaked in 70% ethanol for 1 hour. The demineralized bone sections were cut with scissors to fit into a model M 20 IKA-Universal Mill and processed in the mill for about 30 seconds to produce demineralized bone particles in the form of fibers (yield 17.98 g, 110 cc). The fibers were then frozen and lyophilized for about 12-15 hours.

Comparative Example 119 g of mineralized human donor bone was milled in the milling machine described in U.S. Pat. No. 5,607,269 to provide a quantity of mineralized bone particles in the form of fibers. The mineralized fibers were then subjected to a demineralization process described as follows. Allogenic cortical bone is placed in a reactor. A 0.6 N solution of HCl at 15 ml per gram of bone is introduced into the reactor, the demineralization reaction proceeding for 1 to 2 hours. Following drainage of the HCl, the bone is covered with 0.6 N HCl/20 ppm-2000 ppm nonionic surfactant solution for 24 to 48 hours. Following drainage of the HCl/surfactant solution, 0.6 N HCl at 15 ml per gram of bone is introduced into the reactor, the demineralization reaction proceeding for another 40 to 50 minutes resulting in substantially complete demineralization of the starting cortical bone. Following drainage through a sieve, the demineralized bone is rinsed three times with water for injection at 15 ml per gram bone weight with the water for injection being replaced at 15-minute intervals. Following drainage of the water for injection, the demineralized bone is covered with alcohol and allowed to soak for at least 30 minutes. The alcohol is then drained and the bone is rinsed with water for injection. The demineralized bone is then subdivided in the bone milling apparatus of U.S. Pat. No. 5,607,269 to yield a mass of demineralized bone particles of fibrous configuration. The demineralized bone elements are then drained and transferred to a lyophilization tray and frozen at −70° C. for at least 6 hours. The demineralized bone particles are then lyophilized following standard procedures for 24 to 48 hours. After drying, the demineralized bone particles are sorted for size. The yield of substantially fully demineralized bone particles made following this procedure, as measured before drying, was yield 15.27 g, 75 cc.

The following table compares the yields between the method of Example 1 illustrating the present invention and the prior art method illustrated in the Comparative Example:

|  | Staffing Whole bone | Amount of Product Demineralized Bone Particles | | Wt. % Yield of Demineralized Bone Particles Based on Wt. of |
| --- | --- | --- | --- | --- |
|  | Wt. (g) | Wt. (g) | Vol.(cc) | Whole Bone |
| Example 1 | 99 | 17.98 | 110 | 18.2 |
| Comparative Example | 119 | 15.27 | 75 | 12.8 |

As these data show, the method of this invention in which demineralization of the whole bone precedes its subdivision into demineralized bone particles (Example 1) yielded almost 50 wt. % more useful product than that resulting from the prior art method in which demineralization is conducted only after the whole bone has been subdivided into mineralized bone particles (Comparative Example).

EXAMPLE 2

Substantially fully demineralized fibula cross sections of about 25 mm in length were initially pressed between two flat plates of a Carver press at pressures ranging from 5,000 up to about 20,000 psi. This first pressing operation flattened the bone sections and began to separate their collagen bundles into fibers. This material was then "fluffed up" and pressed again employing similar pressures as before. The pressing operation was again repeated yielding a mass of coarse bundles of fibers that were not completely separated from each other. The yield of fibers was about 50 wt. % based on the volume of the starting demineralized bone sections and many of the fibers possessed lengths that were nearly as great as the natural fibers of the bone stock. The fibers ranged in length from 10-15 mm, with some fibers in the range of from 20-25 mm, and possessed diameters of about 2 mm. Material that was not in fiber form remained in bundled fiber clumps.

The fibers were further subdivided in an impact mill for 30 seconds resulting in a reduction of the diameters of many of the fibers and fiber bundles without, however, significantly reducing their length. Thus, the fibers continued to fall within the aforesaid range of length but their diameters were now within the range of from about 0.5 to about 2 mm.

EXAMPLE 3

Demineralized fibula cross sections, about 25 mm in length, were placed in a series of 29 mm diameter press cells possessing single orifices in their bottoms having diameters of 1, 2 and 3 mm, respectively. Under pressures of from 5,000-10,000 psi, the demineralized bone sections subdivided into fibers which extruded through the orifices. Yields of demineralized fiber were on the order of nearly 100 wt. % in almost every case; little or no bone remained in the cells.

EXAMPLE 4

A cell pressing procedure similar to that of Example 3 was carried out on demineralized bone sections of from 4 to 8 mm in length in a 29 mm diameter press cell having a single orifice of 0.75 mm diameter. At a press load of 5,000 to 10,000 psi, the bone sections subdivided into fibers that ranged in length from 25 to 50% of the length of the bone sections from which they were obtained. Yield of fiber was about 50 wt. %. The fibers ranged in length from about 1-5 mm and possessed a diameter of about 0.5 mm.

EXAMPLE 5

Substantially fully demineralized fibula cross sections of about 25 mm in length were pressed in the press cells described in Example 4. At pressures ranging from 5,000 to 10,000 psi, the bone sections subdivided into fibers having the dimensions set forth in the following table:

| Diameter of Press Cell Orifice, mm | Approximate Length of Fibers, mm | Approximate Diameter of Fibers, mm |
| --- | --- | --- |
| 1 | 1-5 | 1.5-2 |
| 2 | 1-5 | 1.75-275 |
| 3 | 1-5 | 3-3.5 |

EXAMPLE 6

The pressing operations described in Example 5 were substantially repeated but were preceded by a preliminary pressing carried out in a Carver press at 15,000 psi. The resulting demineralized bone fibers possessed smaller diameters, and consequently, greater length to diameter ratios, than the fibers obtained in Example 5.

EXAMPLE 7

Substantially fully demineralized whole fibula shafts were subdivided into fibrous particles employing a Tracer (rotary grater) mill. Fiber length was about 5 mm, diameter was about 0.5 mm and fiber yield was about 70 wt. %.

EXAMPLE 8

Example 7 was repeated but with fibula sections of 4-8 mm in length. Fiber length was about 3-5 mm, diameter was about 0.5 mm and fiber yield was about 50 wt. %.

EXAMPLE 9

A model M5A Fitzpatrick Mill was employed to subdivide substantially fully demineralized bovine bone chips of 4-10 mm into fibrous particles having a length of about 1-2 mm and a diameter of about 0.2-0.7 mm in a yield of about 70 wt. %.

EXAMPLE 10

Example 9 was repeated but employing a model M 20 IKA-Universal Mill to subdivide the demineralized bovine bone chips. The fibers in the fiber-fraction produced by the mill had a length of about 1-2 mm, a diameter of about 0.5-1 mm and the fiber yield was about 10%.

EXAMPLE 11

Example 9 was repeated but employing a Megatron homogenizer (Glen Mills Inc., Maywood, N.J.). The resulting fibers, produced in a yield of about 70 wt. %, possessed a length of about 1-3 mm and a diameter of about 0.2-0.5 mm.

What is claimed is:

1. A method of making demineralized bone particles which comprises demineralizing whole bone and thereafter subdividing the demineralized bone into demineralized bone particles, wherein subdividing of the demineralized bone is carried out by applying pressure to the demineralized bone using a mechanical press, wherein the pressure is applied from about 1,000 to about 40,000 psi.

2. The method of claim 1 wherein the bone is subjected to pressing while unconstrained.

3. The method of claim 2 wherein the product of pressing is subjected to an additional pressing while constrained.

4. The method of claim 1 wherein the bone is subjected to pressing while constrained.

5. The method of claim 1 wherein the product of pressing is subjected to an additional subdividing operation.

6. A method of making demineralized bone particles which comprises demineralizing whole bone and thereafter subdividing the demineralized bone into demineralized bone particles, wherein subdividing of the demineralized bone is carried out by applying pressure to the demineralized bone using a mechanical press, wherein the pressure is applied from about 5,000 to about 20,000 psi.

7. The method of claim 6 wherein the bone is subjected to pressing while unconstrained.

8. The method of claim 7 wherein the product of pressing is subjected to an additional pressing while constrained.

9. The method of claim 6 wherein the bone is subjected to pressing while constrained.

10. The method of claim 6 wherein the product of pressing is subjected to an additional subdividing operation.

* * * * *